(12) United States Patent
Gonzalez et al.

(10) Patent No.: US 6,380,547 B1
(45) Date of Patent: Apr. 30, 2002

(54) TAGGING COMPOSITIONS AND METHODS

(76) Inventors: Manuel E. Gonzalez, 5303 Windy Lake, Kingwood, TX (US) 77345; Roy Goeller, 174 Chamisa, Los Alamos, NM (US) 87544; Jacobo Archuleta, 421 Camino Santa Cruz, Espanola, NM (US) 87532; Dale Spall, 365 Briston Pl., Los Alamos, NM (US) 87544

( * ) Notice: Subject to any disclaimer, the term of this patent is extended or adjusted under 35 U.S.C. 154(b) by 0 days.

(21) Appl. No.: 09/445,622
(22) PCT Filed: Jun. 9, 1998
(86) PCT No.: PCT/US98/11839
§ 371 Date: Dec. 9, 1999
§ 102(e) Date: Dec. 9, 1999
(87) PCT Pub. No.: WO98/57459
PCT Pub. Date: Dec. 17, 1998
(51) Int. Cl.⁷ ............................................... G01N 21/64
(52) U.S. Cl. ............................. 250/458.1; 250/459.1; 250/461.1
(58) Field of Search ........................... 250/461.1, 458.1, 250/459.1

(56) References Cited

U.S. PATENT DOCUMENTS

| | | | | |
|---|---|---|---|---|
| 4,598,205 A | * | 7/1986 | Kaule et al. | 250/458.1 |
| 4,675,529 A | * | 6/1987 | Kushida | 250/458.1 |

* cited by examiner

*Primary Examiner*—Constantine Hannaher
*Assistant Examiner*—Andrew Israel
(74) *Attorney, Agent, or Firm*—John R Casperson

(57) ABSTRACT

A process for marking an article in a manner which is optically invisible and difficult to detect. The process is carried out by selecting a laser luminophore which fluoresces in a predetermined portion of the spectrum when exposed to an excitation light of predetermined wavelength and applying the laser luminophore to the article in an amount which is optically invisible when the article is exposed to electromagnetic radiation but which is sufficient for machine detection when the article is exposed to an excitation light of predetermined wavelength.

14 Claims, 5 Drawing Sheets

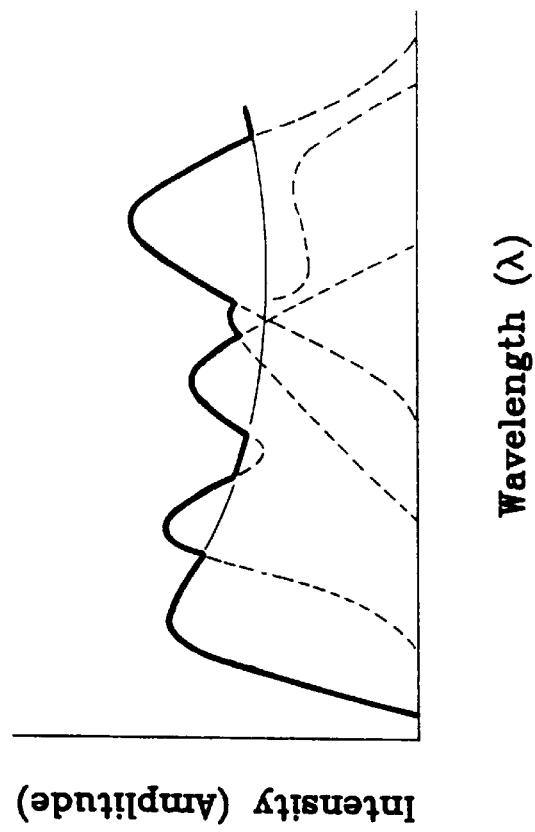
FIG. 3
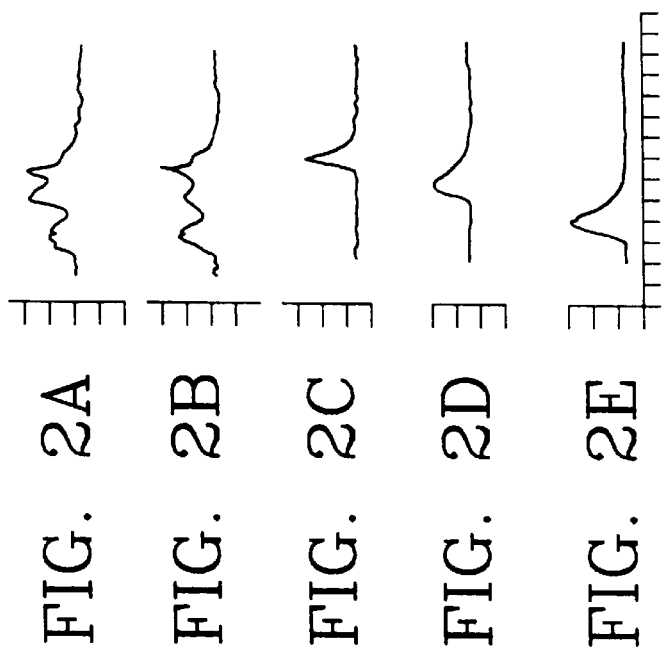
FIG. 2A
FIG. 2B
FIG. 2C
FIG. 2D
FIG. 2E

TAGGING COMPOSITIONS AND METHODS

TECHNICAL FIELD

This invention relates to the use of chemical tags to convey embedded information.

BACKGROUND ART

It can be very useful to be able to determine the source of articles in commerce. For example, governmental entities would often like to be able to determine whether currency is counterfeit, and to produce currency which is difficult to counterfeit. Law enforcement organizations would like to be able to undetectably mark currency used in a ransom, for example, to be able to trace the currency back to a person who placed the marked currency in commerce. Investigators, for example, would like to be able to determine from bomb residue where the materials used entered commerce, so as to be able to determine the purchaser of the components used in the bomb.

Business entities have a need to determine whether goods which are identified with them are authentic. In order to accomplish this, such entities have a need to mark their goods in a manner which is difficult to detect, and difficult to surreptitiously replicate. A solution is especially needed for easily replicated goods, such as those in printed or digital form.

Both business and government have a need to mark materials which they have placed in commerce in a machine readable form to provide a basis for taking future action. For example, currency and many consumer products have a limited life. Machine readable date information would provide a mechanism for removing such goods from commerce at a desirable time in a cost effective manner. Business also have a need from time to time to remove defective goods from commerce. A technique for uniquely labeling goods in a machine readable form would facilitate such removal.

In various aspects, the invention is intended to address these needs.

DISCLOSURE OF INVENTION

In one embodiment of the invention, there is provided a process for marking an article in a manner which is optically invisible and difficult to detect. The process is carried out by selecting a laser luminophore which fluoresces in a predetermined portion of the spectrum when exposed to an excitation light of predetermined wavelength and applying the laser luminophore to the article in an amount which is optically invisible when the article is exposed to electromagnetic radiation but which is sufficient for machine detection when the article is exposed to the excitation light of predetermined wavelength.

In another embodiment of the invention, there is provided a process for placing a chemical "signature" on an article. The process is carried out by selecting a plurality of laser luminophores which fluoresce at different wavelengths in a predetermined portion of the spectrum when exposed to an excitation light of predetermined wavelength and applying the plurality of laser luminophores to a representative article in an amount which is optically invisible when the representative article is exposed to electromagnetic radiation but which is sufficient for machine detection when the representative article is exposed to the excitation light of predetermined wavelength.

The combination of laser luminophores is easily selected to yield a unique fluorescence spectral signature. The location of the peaks can be varied by taggant selection. It also varies depending on the wavelength of the excitation light, and, to some extent, on the carrier media The intensity of the peaks can be varied by taggant concentration. The identity of the taggants can be confirmed by evaluating the spectral signature at different times t after termination of the laser excitation, as well as by chromatograph/mass spec technique. Because the spectral signature obtained will change as the fluorescence decays, the primary spectral analysis should therefore be performed at a predetermined time t after laser excitation is terminated. Unless a counterfeiter has knowledge of the exact laser luminophores utilized, the wavelength of the excitation light employed in the analysis, and the time t at which is primary analysis is performed, replication of the signature would be extremely difficult. If the counterfeiter had knowledge of the time t at which the analysis was to be performed, an attempt could be made to match the signature with other chemicals by varying concentrations. This is easily countered, however, by performing a secondary spectral analysis at a different time t' and comparing to a standard to confirm whether the same laser luminophores were utilized, or alternatively, performing a GC/mass spec analysis. If desired, laser luminophores having rapid decay can also be employed to mask the detection of laser luminophores having slow decay.

In another embodiment of the invention there is provided a method for recording information in machine readable form. The method is carried out by selecting a desired region of the electromagnetic spectrum and dividing it into a plurality of subregions. An information class is assigned to each of the plurality of subregions. Each information class comprises a plurality of information items. A sufficient number of discrete laser luminophores which luminescence in each of the subregions are selected to encrypt the plurality of information items contained within each information class. An encryption code is assigned to each of the information items. The code is selected from nil, one selected laser luminophore, and more than one laser luminophore. An information item is selected from each of at least a portion of the information classes. A multiplicity of laser luminophores which correspond to the selected information items according to the assigned encryption code are then selected and placed in a location from they can be subsequently accessed for exposure to luminescence inducing radiation.

The encryption easily carried out by associating a predetermined information meaning with peak locations in the luminescence spectrum. For convenience, the spectrum can be separated into regions and predetermined information meanings assigned to peaks appearing in the regions. For example, a great many laser luminophores display fluorescence in the region of 300–1000 nm. This spectral region can be divided into portions and each portion used to carry a different information item. Ten laser luminophores which display distinguishable fluorescence peaks in the range of 300–450 nm can be used to designate different years. Twelve laser luminophores which display distinguishable fluorescence peaks in the range 800–1000 nm can be used to designate different months. Thirty laser luminophores which display distinguishable fluorescence peaks in the range 450–550 nm can be used to designate different companies. Thirty laser luminophores which display distinguishable fluorescence peaks in the range of 550–650 nm can be used to designate thirty manufacturing or distribution plants. Thirty one laser luminophores which display distinguishable fluorescence peaks in the range of 650–800 nm can be used to designate days in months. Peaks may be distinguishable by lambda(max), by intensity, by shape, and/or by decay characteristics.

Combinations of laser luminophores which display fluorescence in the desired region may also be used, and this greatly reduces the number of luminophores which display fluorescence in the desired region and the resolution capabilities needed to carry out this aspect of the invention. For example, a luminophore A which display fluoresce at 580 nm, a luminophore B which displays fluorescence at 580 nm, a luminophore C which displays fluorescence at 600 nm, a luminophore D which displays fluorescence at 620 nm and a luminophore E which displays fluorescence at 640 nm can be used in varying combinations and subcombinations to yield 30 spectral signatures (A, B, C, D, E, AB, AC, AD, AE, BC, BD, BE, CD, CE, DE, ABC, ABD, ABE, ACD, ACE, ADE, BCD, BDE, CDE, ABCD, ABCE, ABDE, ACDE, BCDE, ABCDE) in the region of 550–650 nm.

Bar codes typically contain 10 digits, typically integers of from 0 to 9. Four luminophores are required to encrypt 10 information units. For example, luminophores A, B, C and D, each displaying fluorescence peaks separated by about 15 nm, can be employed to encrypt the integers digits 0–9 by utilizing the subcombinations A, B, C, D, AB, AC, AD, ABC, ABD, ACD. The spectral range of 350–950 nm can be divided into 10 regions of 60 nm each and 4 such luminophores selected for each region The resulting system constitutes a chemical machine-readable "bar code".

The encryption can be totally of binary form if desired. Each luminophore, by its presence or absence, would be employed to encrypt two information units, typically 0 or 1. The spectral range of 350–950 nm could be divided up into 40 portions of 15 nm width each. The number of unique encryption possibilities is $2^{40}$ power by this scheme, which is on the order of a trillion possibilities. The number of possibilities can be further increased by utilizing a larger portion of the fluorescence spectrum, or by further subdividing the spectral range by improved resolution techniques, or by layering the encryption information in each portion of the spectrum based on luminophore decay rate. For example, rapidly decaying luminophores A, B, C and D can be used to encrypt any first integers 0–9 in a spectral region, and slowly decaying luminophores A', B', C' and D' can be used to encrypt any second integer 0–9 (which can be same as or different from the first integer) in the same spectral region. The second information item is retrieved by detecting the fluorescence at a later time t than the first information item.

In another embodiment of the invention there is provided a composition of matter comprising a carrier medium, and a multiplicity of laser luminophores in the carrier medium. Each of the multiplicity of laser luminophores luminesces within the spectral range of 300–1000 nm and each laser luminophore is spectrally distinguishable from the other laser luminophores by its luminescence characteristics. At least one laser luminophore exhibits a spectral peak within each of the spectral ranges of 300–550 nm, 550–750 nm and 750–1000 nm.

The just described multiplicity of laser luminophores can also be used to provide a machine readable label by impregnating them on substrate sheet suitable for use as a label, according to a further embodiment of the invention.

In yet another embodiment of the invention, there is provided a composition of matter which contains a further level of encryption at the molecular level. The composition is formed by a carrier medium containing at least one laser luminophore. The laser luminophore contains at least one non-radioactive isotopic atom in an amount which is not naturally occurring.

In this embodiment of the invention, a secondary level of encryption can be carried out by utilizing tagging agents which have been isotopically enriched at one or more locations in the molecule, such as by deuterium labeling, and evaluating the mass spectrum for characteristic peaks indicative of molecular fragments carrying a non-naturally occurring distribution of isotopic atoms.

In yet another embodiment of the invention, there is provided a process for detecting a laser luminophore carried in or on a medium. The laser luminophore emits a fluorescence spectrum which has at least one characterizing peak when irradiated by an exciting light. The medium is exposed to the exciting light so as to cause said laser luminophore to emit its fluorescence spectrum. At least the characterizing peak in the fluorescence spectrum is detected. The invention is characterized in that the characterizing peak is in the spectral range of about 600 to about 2500 nm, and the exciting light has a wavelength in the range of about 200 to about 600 nm.

In another embodiment of the invention, there is provided a process for reading information encrypted into or onto a medium by a plurality of discrete laser luminophores. Each of the discrete laser luminophores is characterized by emission of a fluorescence spectrum in response to exposure to exciting light which has at least one characterizing peak which differentiates its spectrum from the spectra of the other discrete laser luminophores of the plurality. The process is carried out by exposing the medium to exciting light so as to cause the plurality of discrete laser luminophores to emit their respective fluorescence spectra. A predetermined portion of the emitted spectrum is analyzed in a first portion of a fluorescence analysis. A first information meaning is assigned to the results of the first portion of the fluorescence analysis according to a first according to a first encryption correlation. A predetermined portion of the emitted spectrum is then analyzed in a second portion of a fluorescence analysis. A second predetermined information meaning is assigned to the results of the second portion of the fluorescence analysis according to a second encryption correlation.

In still another embodiment of the invention, there is provided a process for sorting articles based on the use of laser luminophores. There is provided a stream of articles at least a portion of which carry a combination of laser luminophores which emit a fluorescence spectrum in response to exposure to exciting light. The stream of articles is exposed to exciting light, one at a time, so as to cause the combination of laser luminophores carried by any one of the articles to emit a fluorescence spectrum. For each of the articles which emit the fluorescence spectrum, a plurality of peak locations in the emitted fluorescence spectrum is determined. These peak locations are then correlated with information selected from the group consisting of binary information, alpha-numeric information, date information, and origin information. The articles are then sorted based on the correlation.

BRIEF DESCRIPTION OF DRAWINGS

FIG. 2 illustrates the individual spectra of several tags in graphs A, B, C, D and E.

FIG. 3 illustrates a combined spectrum curve resulting from adding together the tags shown in FIG. 2 in the form of a spectrogram. FIGS. 2 and 3 together illustrate how several tags can be added together to yield a combined spectrum curve.

BEST MODE FOR CARRYING OUT THE INVENTION

Figure 1:
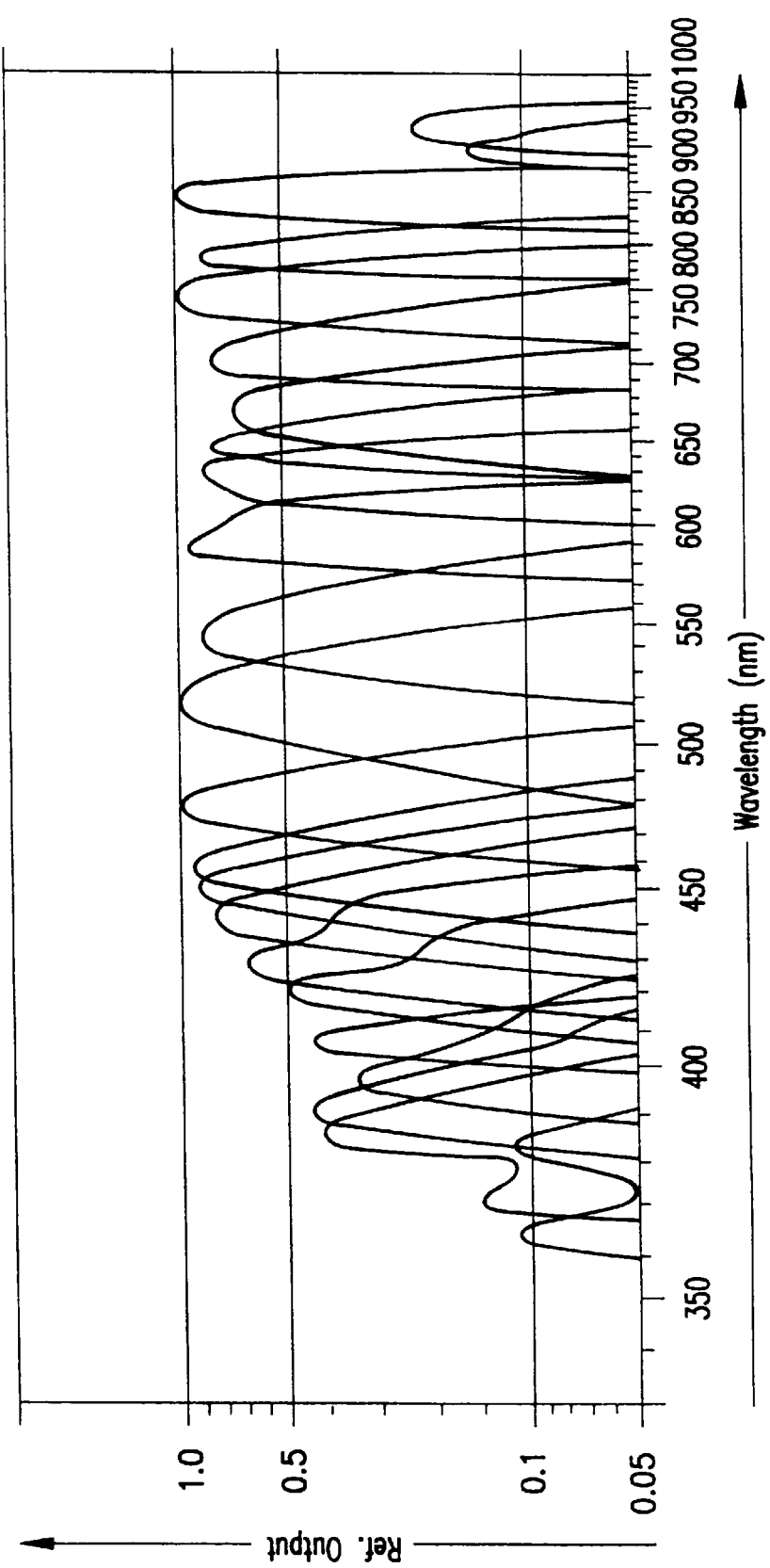
FIG. 1 illustrates, on a single graph, the fluorescence spectra of some typical Organic Fluorescent Dyes.
Figure 4:
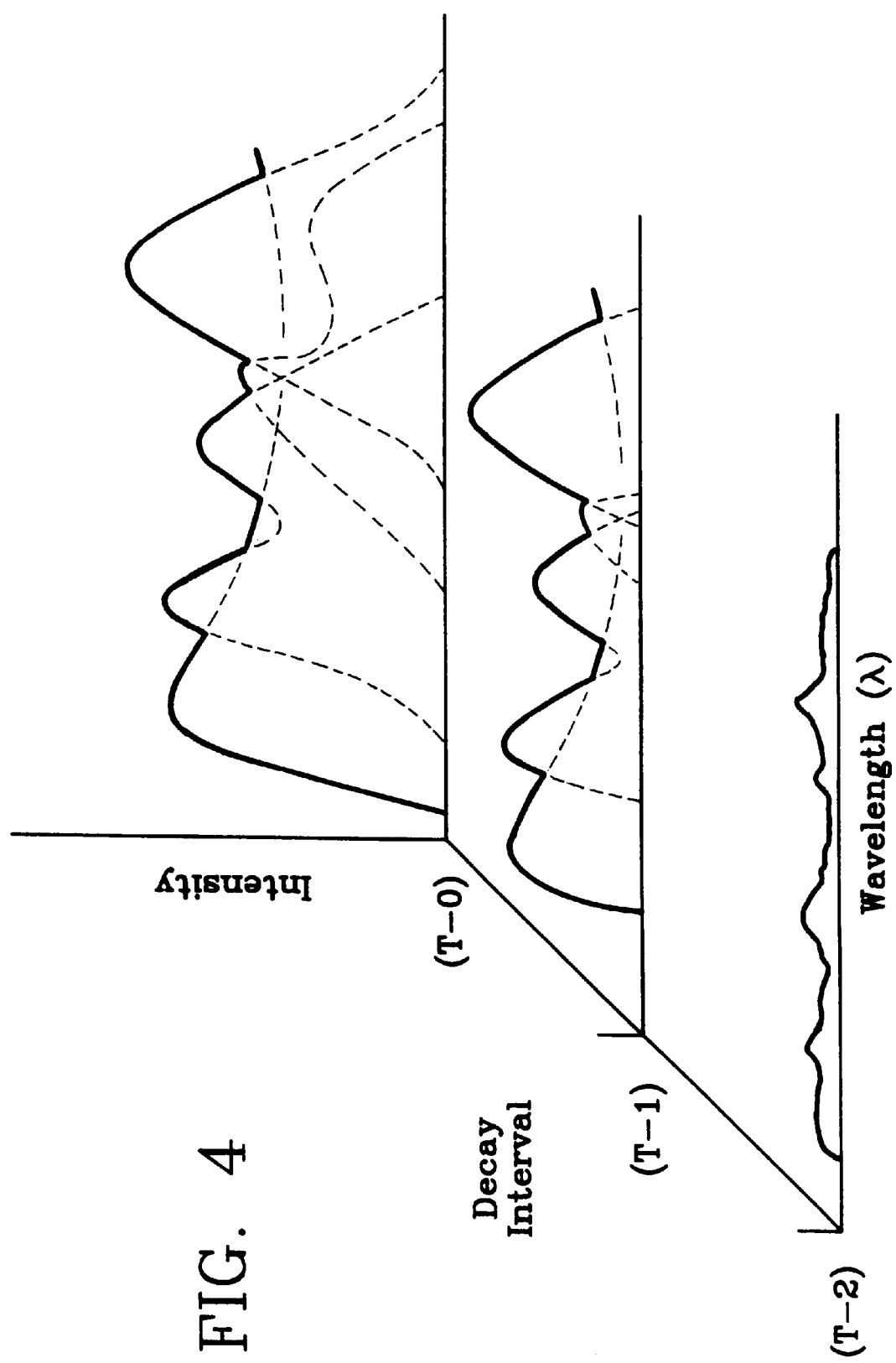
FIG. 4 is a three dimension spectrum to illustrate how a fluorescence spectral curve can change over time.
Figure 5:
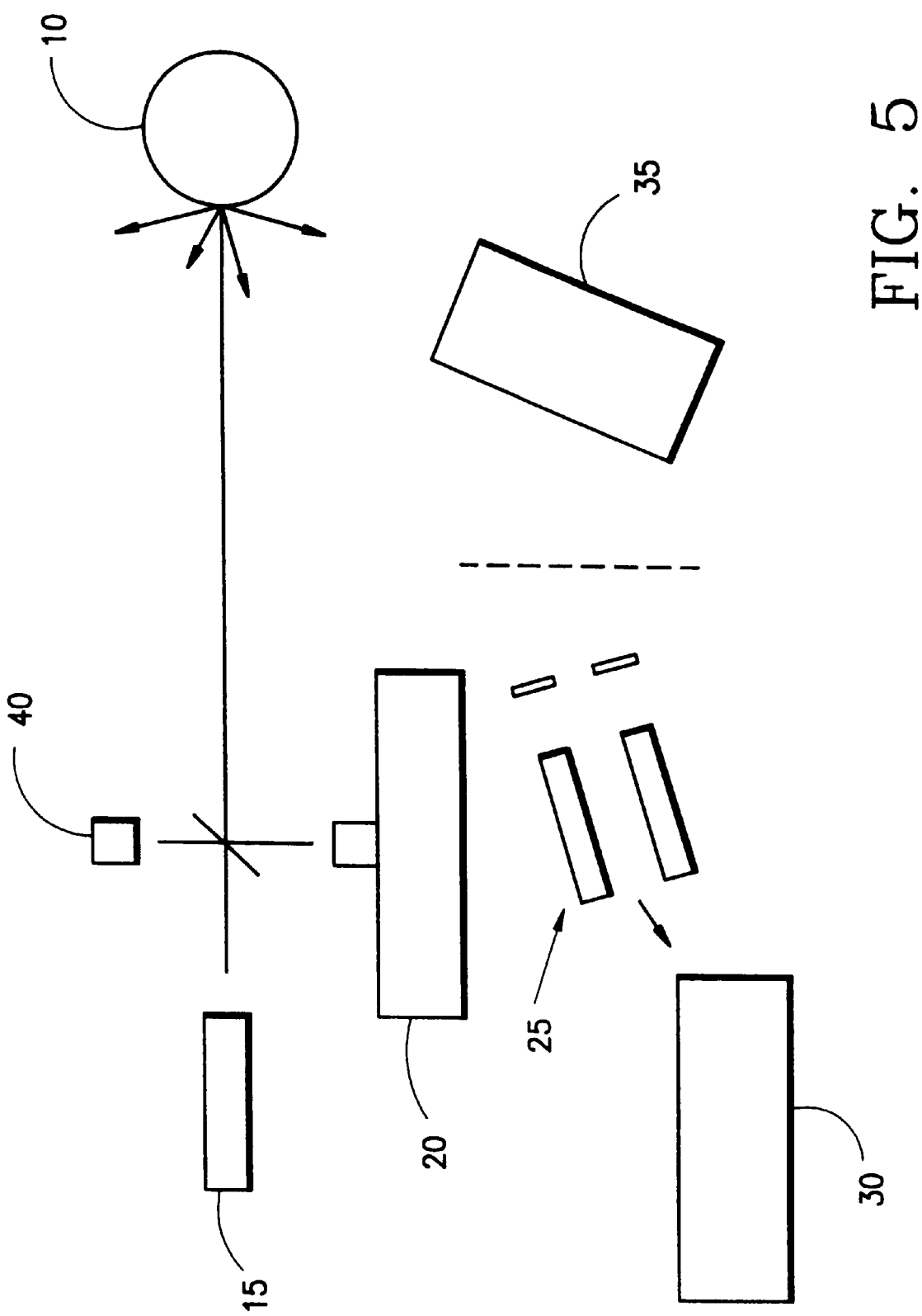
FIG. 5 schematically illustrates detector arrangements The vertical dashed line separates a fluorescent tag detection portion of the device on the left, which provides a fast ID bar-code readout with high sensitivity from a bar code reading portion of the device to the right of the dashed line which represents a slower ID bar-code reader using the time domain with high resolution and low sensitivity. An operative relationship between target 10, UV laser scanner 15, background monitor 20, filters and detectors 25, an electronics and logic display 30, a spectrometer with display 30, and a laser monitor 40 is shown.
Figure 6:
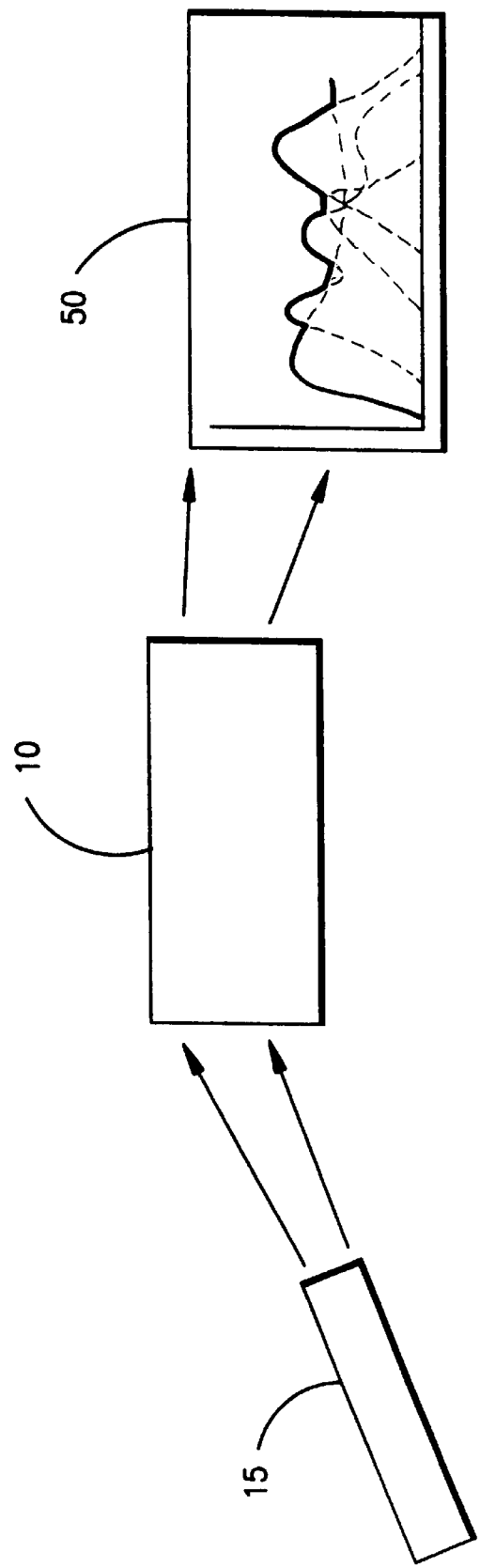
FIG. 6 schematically illustrates the detection process. Laser 15 impinges on target 10, causing fluorescence of different flurophores, which results in the production of combined spectrum 50.

Laser luminophores are well known. They are usually polycyclic chemical compounds. They are usually characterized as fluorescent, although they continue to emit light after excitation for periods of time ranging from a few nanoseconds up to several hundred milliseconds after the exciting light is terminated and are therefor probably more accurately classed as phosphors. Suitable laser luminophores are articles of commerce for laser pumped dyes and are sold, for example, by Lambda Physik, Hans-Boeckler-Strasse 12, D-37079 Goettingen, Germany and Lambda Physik Inc., 3201 West Commercial Blvd., Ft. Lauderdale, Fla. 33309.

Preferred laser luminophores display their fluorescence in the range of 300–2500 nm and have a peak width of less than about 200 nm. Particularly preferred laser luminophores display their fluorescence in the range of 350–1000 nm, and have a peak width of less than 100 nm More preferred laser luminophores are those which have an even narrower peak width. Laser luminophores are optically invisible under common lighting conditions such as daylight, incandescent light and fluorescent light, when applied to a substrate in an amount which is machine detectable following laser induced excitation are also more preferred. The most preferred laser luminophores are those which remain optically invisible even under exposure to electromagnetic radiation, such as a black light, ie. they are machine-detectable only in the amounts in which they are used.

For many applications, it is desirable to select laser luminophores which fluoresce in an upper portion of the above described region, to reduce the chances of interference with any fluorescence which is inherent to the composition of the material being tagged. Laser fluorophores which generally luminesce in the region of about 600 to about 2500 nm are preferred for such applications. Laser luminophores which luminesce in the region of about 650 to about 1500 are more preferred, and those which luminesce in the region of about 700 to about 1200 nm are particularly preferred.

Laser luminophores emit their fluorescence at a wavelength which is longer than the wavelength of the fight which is used to induce the fluorescence.

In one embodiment of the invention, It is most preferred to induce the fluorescence with laser light, because it is very intense and controlled, and provides a measurable response from extremely small amounts of laser luminophores. The preferred portion of the spectrum to use for analysis purposes in the invention is in the range of 350–1,000 nm, because a large number of suitable laser luminophores are known which fluoresce in this region. The most preferred laser light sources thus emit light having a wavelength of less than about 300 nm. However, a sufficient number of suitable luminophores are available so that the invention can be satisfactorily carried out by employing laser light sources emitting in the 200 to 600 nm range, preferably in the 230 to 500 nm range, and more preferably in the 235 to 470 nm range. Suitable most preferred sources include XeCl-Excimer laser (309 nm), Nitrogen laser (337 nm) and Nd:YAG, 3rd (355 nm). A suitable laser source will often have an intensity in the range of from about 1 to about 100 microjoules and a duration in the range of from about 1 to about 10 nanoseconds.

In another embodiment of the invention, it is preferred to induce the fluorescence with a solid state light source, such as a light emitting diode (LED). Preferred LED light sources generally emit light having a wavelength in the range of about 400 to about 600 nm, preferably in the range of about 430 to about 590 nm, and most preferably in the range of about 450 to about 500 nm. Because light from an LED source is less intense than light from a laser source, it is preferred to carry out the excitation in this embodiment of the invention by employing a plurality of LED sources. For example, a detector having in the range of 2 to 10 light emitting diodes will provide good results. Because suitable LED light sources generally emit their light at a longer wavelength than the laser sources, they are most preferably employed in conjunction with the laser luminophores which fluoresce in the 600–2500 range as described above.

Detectors suitable for use in the invention are well within the grasp of one skilled in the art. Generally speaking, the excitation light is impinged on the target and the resulting fluorescence is detected by one or more light detectors off to the side of the target. Photomultiplier tubes make excellent detectors. Filters are positioned between the target and the photomutiplier tubes to screen out light having a wavelength other than the wavelength of interest. Bandpass filters are highly suitable for this purpose. To carry out the invention with equipment of this type, a photomultiplier tube with specific filter would be used for each wavelength to be detected. Photo diodes, which are solid state devices, are also highly suitable, and are commercially available with built in amplifiers. Alternatively, the entire fluorescence spectrum over the region of interest can be collected in a known manner, and this would be preferred where the objective is to obtain a spectral signature. Timers can be employed to detect or measure the light emitted by the flurophores at a desired time.

The presence or absence of a flurophores can thus be determined by equipment well known in the art. This information can be processed further by computer to carry out for carrying out remaining aspects of the invention The necessary algorithms can readily be prepared by those of ordinary skill in the art without undue experimentation. They will generally include comparing the detected taggant wavelength to a "table" containing a plurality of taggant wavelengths and associated information maintained in the system memory and establishing control signals responsive to the comparison.

In one embodiment of the invention, there is provided a process for marking an article in a manner which is optically invisible and difficult to detect. The process is carried out by selecting a laser luminophore which fluoresces in a predetermined portion of the spectrum when exposed to an excitation light of predetermined wavelength and applying the laser luminophore to the article in an amount which is optically invisible when the article is exposed to electromagnetic radiation but which is sufficient for machine detection when the article is exposed to the excitation light of predetermined wavelength.

This embodiment of the invention is particularly useful for marking paper currency, copyrighted works of authorship such as computer programs, videocassette recordings, CD-ROMs, books, and labels. Generally speaking, the laser luminophore is applied to the article in a very small amount, generally less than 1 ppm, based on the weight of the article. The luminophore is preferably selected so that it is distinguishable at some time t after the exciting excitation light is terminated, from any other luminophores already present on the article. Preferably, the laser luminophore fluoresces at a wavelength in the range of about 350 nm to about 1000 nm when exposed to excitation light having a wavelength in the range of about 250 nm to about 350 nm.

A secondary level of encryption can be achieved by employing a laser luminophore which contains a non-radioactive isotopic atom in an amount which is not naturally occurring. A deuterated luminophore is preferred for this purpose. The amount and location of the deuteration can be arbitrary, rendering replication extremely difficult. The deuterated laser luminophore will display a mass spectrum signature which is easily distinguishable from non deuterated luminophores, or luminophores which have been deuterated in different amounts or locations. A gas chromatograph/mass spec analysis of a sample of luminophore which has been recovered from the marked article is the preferred way of making the required determination.

The luminophore is easily "hidden" on the article which it marks. If desired, the laser luminophore is selected so as to be masked by fluorescence inherent to the composition of the article when the article is exposed to the excitation light of predetermined wavelength but is machine detectable after the passage of a period of time sufficient to permit the fluorescence inherent to the composition of the article to decay. The time of detection will generally range from a few nanoseconds to several hundred millisecond after the cessation of the laser illumination.

Application of the laser luminophore to the article can be via a variety of techniques. Generally, the luminophore will be dissolved in a liquid carrier such as an ink or an evaporative solvent and the liquid applied to the article to be marked. A technique to result in the luminophore being impregnated onto a portion of the article in a manner so that it is difficult to remove is preferred.

In another embodiment of the invention, there is provided a process for placing a chemical "signature" on an article. The process is carried out by selecting a plurality of laser luminophores which fluoresce at different wavelengths in a predetermined portion of the spectrum when exposed to an excitation light of predetermined wavelength and applying the plurality of laser luminophores to a representative article in an amount which is optically invisible when the representative article is exposed to electromagnetic radiation but which is sufficient for machine detection when the representative article is exposed to the excitation light of predetermined wavelength.

The desired fluorescence "signature" can be obtained by exposing the representative article to the excitation light of predetermined wavelength and obtaining the fluorescence spectrum resulting from such exposure. The fluorescence spectrum is stored for subsequent access, generally either on paper or in computer memory. Because the signature will vary depending on the wavelength of the excitation light used, the wavelength of the excitation light used to obtain the signature should also be stored. Also, because the signature will vary depending on the decay characteristics of the luminophores used, the time at which the signature is taken should also be stored. The decay characteristics of the luminophores can also be used to safeguard against surreptitious replication of the signature. This can be accomplished by obtaining a second florescence spectrum at a second time t2 after the termination of the excitation light exposure and storing the second fluorescence spectrum for subsequent access.

A complex signature will be more difficult for a counterfeiter to replicate than a simple one. It is thus preferred to employ several luminophores to make the signature. Generally speaking, at least three laser luminophores, preferably at least five laser luminophores, are applied to the representative article. Suitable luminophores can be as previous described. If desired, at least one of the laser luminophores can contain at least one non-radioactive isotopic atom in an amount which is not naturally occurring, in a manner as previously discussed. When this is done, a mass spectrum of each of the at least one laser luminophore which contains at least one non-radioactive isotopic atom in an amount which is not naturally occurring should be taken and stored for subsequent access.

A different combination of laser luminophore can be applied to each type of article to be marked. For this purpose, it is preferred to select the plurality of laser luminophores to uniquely identify articles represented by the representative article and to apply the plurality of laser luminophores solely to articles represented by the representative article, preferably in a permanent manner, that is, in a manner so they cannot be removed without damaging the article. The invention can generally be carried out with small amounts of luminophores, generally less than by 10 parts per million each, based on the weight of the article.

To determine whether an article taken from commerce is represented by the representative article, it is exposed to an excitation light having the predetermined wavelength and a florescence spectrum obtained under generally the same conditions as for the representative article. The fluorescence spectrum thus obtained is compared to the first fluorescence spectrum. This can be done by computer if desired. Authenticity, or lack thereof can be determined by obtaining a second florescence spectrum at the second time after the termination of such exposure, and comparing the spectrum thus obtained with the second fluorescence spectrum, and/or by mass spectrometer, particularly where at least one of the laser luminophores employed contains at lest one non-radioactive isotopic atom in an amount which is not naturally occurring.

In another embodiment of the invention there is provided a method for recording information in machine readable form. The method is carried out by selecting a desired region of the electromagnetic spectrum and dividing it into a plurality of subregions. An information class is assigned to each of the plurality of subregions. Each information class comprises a plurality of information items. A sufficient number of discrete laser luminophores which luminescence in each of the subregions are selected to encrypt the plurality of information items contained within each information class. An encryption code is assigned to each of the information items. The code is selected from nil, one selected laser luminophore, and more than one laser luminophore. An information item is selected item from each of at least a portion of the information classes. A multiplicity of laser luminophores which correspond to the selected information items according to the assigned encryption code are then selected and placed in a location from they can be subsequently accessed for exposure to luminescence inducing radiation.

The laser luminophores can have the characteristics and be used as previously. The meaning of the information which is encrypted will generally be independent of some inherent property of the composition being marked. For example, the information classes can be selected from the group consisting of 0 and 1, alpha and numeric, or indicative of manufacturer, location of manufacture, year of manufacture, lot number of product, or recycle information Liquids, plastics, and translucent materials can be labeled in accordance with this embodiment of the invention, as well as substrates such as those suitable for forming labels, such as paper, or generally most any carrier medium from which the laser luminophores may subsequently accessed by extraction technique, such as a solvent extraction, if it cannot be read directly.

In another embodiment of the invention there is provided a composition of matter comprising a carrier medium, and a multiplicity of laser luminophores in the carrier medium. Each of the multiplicity of laser luminophores luminesces within the spectral range of 300–1000 nm and each laser luminophore is spectrally distinguishable from the other laser luminophores by its luminescence characteristics. At least one laser luminophore exhibits a spectral peak within each of the spectral ranges of 300–550 nm, 550–750 nm and 750–1000 nm, preferably when irradiated with excitation light having a wavelength shorter than about 300 nm. The carrier medium and laser luminophores can have the characteristics as previously discussed. More preferably, at least 5 laser luminophores are employed which fluoresce in at least 5 different regions, for example, at least one each in the spectral ranges of 300–450 nm, 450–550 nm, 550–650 nm, 650–800 nm, and 800–1000 nm. This same scheme can be employed to produce a machine readable label by impregnating the selected luminophores on substrate sheet suitable for use as a label, according to a further embodiment of the invention.

In yet another embodiment of the invention, there is provided a composition of matter which contains a further level of encryption at the molecular level. The composition is formed by a carrier medium containing at least one laser luminophore. The laser luminophore contains at least one non-radioactive isotopic atom in an amount which is not naturally occurring.

It is recognized that isotopes are naturally occurring substances and it is not intended to encompass within this embodiment of the invention a carrier medium which contains a molecule containing a non-radioactive isotopic atom in an amount which is not naturally occurring, since any carrier medium which contains a measurable quantity of laser luminophores will contain many such molecules. What is intend to be covered is the situation where the luminophore has been synthesized or treated to impart to it an unnaturally occurring content of isotopes. Generally speaking, the compositions constituting this embodiment of the invention will contain measurable concentration of such luminophores, usually at least one part per trillion by weight. Preferably, the composition contains a sufficient amount of non-radioactive isotopic atoms so that the presence of a non-naturally occurring distribution of such atoms can be determined a by mass spectrometer.

Using present technology, utilizing a concentration in the range of using a concentration in the range of one part per trillion to 100 parts per million is expected to be operable, preferably in the range of 100 parts per trillion to 1 part per million. Deuterium is the isotope of choice, because it is readily available, easily detected, and easy to incorporate into the luminophore. Depending on the deuteration conditions employed, the deuterium content of the luminophores can vary over a wide range, making replication of the mass spec signature very difficult.

If desired, the "doped" laser luminophore can be employed with at least one second laser luminophore contained in the carrier medium in an amount to result in a concentration of the at least one second laser luminophore of at least one part per trillion, by weight, which amount consists of isotopic atoms in naturally occurring amounts.

In another embodiment of the invention, there is provided a process for reading information encrypted into or onto a medium by a plurality of discrete laser luminophores. Each of the discrete laser luminophores is characterized by emission of a fluorescence spectrum in response to exposure to exciting light which has at least one characterizing peak which differentiates its spectrum from the spectra of the other discrete laser luminophores of the plurality. The process is carried out by exposing the medium to exciting light so as to cause the plurality of discrete laser luminophores to emit their respective fluorescence spectra. A predetermined portion of the emitted spectrum is analyzed in a first portion of a fluorescence analysis. A first information meaning is assigned to the results of the first portion of the fluorescence analysis according to a first according to a first encryption correlation. A predetermined portion of the emitted spectrum is then analyzed in a second portion of a fluorescence analysis. A second predetermined information meaning is assigned to the results of the second portion of the fluorescence analysis according to a second encryption correlation.

Usually, a first predetermined portion of the spectrum is analyzed in the first portion of the fluorescence analysis and a second predetermined portion of the spectrum is analyzed in the second portion of the fluorescence analysis. Alternatively, the same predetermined portion of the spectrum can be analyzed at different times where laser luminophores having different decay characteristics have been employed.

In one aspect, each of the first and second portions of the fluorescence spectrum are analyzed for fluorescence peaks, and each of the first and second portion of the fluorescence spectrum contains more than one peak. For this, it is preferred that each of the first and second portions of the fluorescence spectrum has a band width of more than 100 nm. In another aspect, each of the first and second portions of the fluorescence spectrum are analyzed for fluorescence peaks, and each of the first and second portion of the fluorescence spectrum contains either zero or one peak. For this, it is preferred that each of the first and second portions of the fluorescence spectrum has a band width of less than 100 nm. In another aspect, each of the first and second portions of the fluorescence spectrum are analyzed for fluorescence peaks, and each of the first and second portion of the fluorescence spectrum contains from zero to five peaks. For this, it is preferred that each of the first and second portions of the fluorescence spectrum has a band width of less than 100 nm.

The encrypted information will generally relate to an information item other than some inherent property of the material being tagged. For example, the first information meaning can be selected from the group consisting of 0 and 1, alpha and numeric, or correlate to manufacturer, location of manufacture, year of manufacture, or lot number of product.

In still another embodiment of the invention, there is provided a process for sorting articles based on the use of laser luminophores. There is provided a stream of articles at least a portion of which carry a combination of laser luminophores which emit a fluorescence spectrum in response to exposure to exciting light. The stream of articles is exposed to exciting light, one at a time, so as to cause the combination of laser luminophores carried by any one of the articles to emit a fluorescence spectrum. For each of the articles which emit the fluorescence spectrum, a plurality of peak locations in the emitted fluorescence spectrum is determined. These peak locations are then correlated with information selected from the group consisting of binary information, alpha-numeric information, date information, and origin information. The articles are then sorted based on the correlation. The combination of laser luminophores, the encrypted information, and the articles to be sorted can have characteristics as previously discussed.

The chemical classes of compounds useful as flurophores in accordance with the invention include:

polycyclic hydrocarbons, including catacondensed and pericondensed aromatics as well as substituted member;

heterocyclic hydrocarbons, including condensed and substituted indoles, oxazoles, oxadiazoles and furan compounds; and xanthono and xanthonone derivative, including condensed systems, acids and salts.

Representative laser luminophores with selected CAS numbers suitable for use in the invention are:

p-quatraphenyl 135-70-6 2,3,5,6-1H,4H-tetrahydro-9-acetylquinolizino-[9,9a,1-gh]coumarin 55804-67-6 N-methyl-4-trifluoromethylpiperidino-[3,2-g]-coumarin 55318-19-7 Disodium fluorescein 518-47-8 9-(o-carboxyphenyl)-2,7-dichloro-6-hydroxy-3H-xanthen-3-on 76-54-0 o-(6-amino-3-imino-3H-xanthen-9-yl)-benzoic acid 13558-31-1 benzoic acid, 2-[6-(ethylamino)-3-(ethylimino)-2,7-dimethyl-3H-xanthen-9-yl], perchlorate 62669-66-3 benzoic acid, 2-[6-(ethylamino)-3-(ethylimino)-2,7-dimethyl-3H-xanthen-9-yl]-ethyl ester, monohydrochloride 989-38-8 2-[6-ethylamino)-3-(ethylimino)-2,7-dimethyl-3H-xanthen-9-yl]benzoic acid 81-88-9 8-(2-caarboxyphenyl)-2,3,5,6,11,12,14, 15-octahydro-1H,4H,10H,13H-diquinolizino[9, 9a,1-bc:9a',1-hi]xanthylium perchlorate 64339-18-0

8-(2,4-disulfophenyl)-2,3,5,6,11,12,14,15-octahydro-1H, 4H,10H,13H-diquinolizino[9, 9a,1-bc:9'.9a',1-hi] xanthene no cas 9-diethylamino-5H-benzo(a) phenoxazin-5-one 7385-67-3 1-ethyl-4-(p-dimethylaminophenyl)-1,3-butadineyl)-pyridinium perchlorate no cas 3,3'-diethylthiatricarbocyanine iodide 3071-70-3 3,3'-diethyl-9,11-neopentylenethiatricarbocyanine iodide no cas 1,2'-diethyl-4,4'-dicarbocyanine iodide no cas

What is claimed is:

1. A process for detecting a laser luminophore carried in or on a medium, wherein such laser luminophore emits a fluorescence spectrum which has at least one characterizing peak when irradiated by an exciting light;

said process comprising:

providing a medium carrying, in or on the medium, a laser luminophore suitable for use as a laser pumped dye, exposing said medium to said exciting light so as to cause said laser luminophore to emit its fluorescence spectrum, and detecting at least the characterizing peak in the fluorescence spectrum;

characterized in that the characterizing peak is in the spectral range of about 600 to about 2500 nm, and the exciting light has a wavelength in the range of about 200 to about 600 nm.

2. A process as in claim 1 further characterized in that the exciting fight is from a laser fight source.

3. A process as in claim 2 further characterized by the characterizing peak being in the spectral range of about 650 to about 1500 nm, and the exciting light having a wavelength in the range of about 230 to about 500 nm.

4. A process as in claim 3 further characterized by the characterizing peak being in the spectral range of about 700 to about 1200 nm, and the exciting light having a wavelength in the range of about 237 to about 470 nm.

5. A process as in claim 4 further characterized by the exciting light having a wavelength in the range of about 237 to about 355 nm.

6. A process as in claim 4 further characterized by the detection being carried out by a solid state detection device.

7. A process as in claim 5 wherein the luminophore is carried on a label and the laser luminophore is present in an optically invisible amount.

8. A process as in claim 1 further characterized in that the exciting light is from a light emitting diode source and has a wavelength in the range of from about 400 to about 600 nm.

9. A process as in claim 8 further characterized by the characterizing peak being in the spectral range of about 650 to about 1500 nm, and the exciting light having a wavelength in the range of about 430 to about 590 nm.

10. A process as in claim 9 further characterized by the characterizing peak being in the spectral range of about 700 to about 1200 nm, and the exciting light having a wavelength in the range of about 450 to about 500 nm.

11. A process as in claim 10 further characterized by the exciting light being emitted from a plurality of light emitting diode sources.

12. A process as in claim 11 further characterized by the detection being carried out by a solid state detection device.

13. A process as in claim 12 wherein the luminophore is carried on a label in an optically invisible amount.

14. A process for reading information encrypted into or onto a medium by a plurality of discrete laser luminophores, wherein each discrete laser luminophore is characterized by emission of a fluorescence spectrum in response to exposure to exciting light which has at least one characterizing peak which differentiates its spectrum from the spectra of the other discrete laser luminophores of the plurality of discrete laser luminophores, said process comprising:

exposing said medium to exciting fight so as to cause said plurality of discrete laser luminophores to emit their respective fluorescence spectra, analyzing a predetermined portion of the spectrum in a first portion of a fluorescence analysis;

assigning a first information meaning to the results of the first portion of the fluorescence analysis, wherein the first information meaning is assigned to the results of the first portion of the fluorescence analysis according to a first encryption correlation;

analyzing a predetermined portion of the spectrum in a second portion of a fluorescence analysis; and assigning a second predetermined information meaning to the results of the second portion of the fluorescence analysis, wherein the second information meaning is assigned to the results of the second portion of the fluorescence analysis according to a second encryption correlation.

* * * * *